US008951785B2

(12) United States Patent
Fatherazi et al.

(10) Patent No.: US 8,951,785 B2
(45) Date of Patent: Feb. 10, 2015

(54) STIRRER FOR A BIOREACTOR (75) Inventors: Shahmir Fatherazi, Aachen (DE);
Gerhard Greller, Goettingen (DE);
Oscar-Werner Reif, Hannover (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 936 days.

(21) Appl. No.: 13/129,700

(22) PCT Filed: Oct. 19, 2009

(86) PCT No.: PCT/EP2009/007474
§ 371 (c)(1),
(2), (4) Date: May 17, 2011

(87) PCT Pub. No.: WO2010/057555
PCT Pub. Date: May 27, 2010

(65) Prior Publication Data
US 2011/0229963 A1 Sep. 22, 2011

(30) Foreign Application Priority Data
Nov. 20, 2008 (DE) .......................... 10 2008 058 338

(51) Int. Cl.
*C12M 1/00* (2006.01)
*C12M 3/00* (2006.01)
*B01F 7/00* (2006.01)
*B01F 15/00* (2006.01)
*C12M 1/06* (2006.01)

(52) U.S. Cl.
CPC ....... *B01F 7/00058* (2013.01); *B01F 15/00707* (2013.01); *B01F 15/00831* (2013.01); *B01F 15/0085* (2013.01); *C12M 27/02* (2013.01)
USPC ....................................... 435/289.1; 366/343

(58) Field of Classification Search
CPC ............. B01F 7/00058; B01F 15/0085; B01F 15/00831; B01F 15/00707; C12M 27/02
USPC ........................................ 435/289.1; 366/343
See application file for complete search history.

(56) References Cited

U.S. PATENT DOCUMENTS

| 857,683 A | 6/1907 | Stern et al. |
|---|---|---|
| 1,661,255 A | 3/1928 | Haywood |
| 2,045,710 A | 6/1936 | Haywood |
| 6,769,800 B1 | 8/2004 | Young |
| 2002/0105856 A1 | 8/2002 | Terentiev |
| 2011/0013474 A1* | 1/2011 | Ludwig et al. ................ 366/102 |

OTHER PUBLICATIONS

International Preliminary Report on Patentability, Issued on May 31, 2011.

* cited by examiner

*Primary Examiner* — Michael Hobbs
(74) *Attorney, Agent, or Firm* — Gerald E. Hespos; Michael J. Porco; Matthew T. Hespos (57) ABSTRACT A stirrer for a bioreactor has first and second opposed mountings fastened to the inner surfaces of opposite walls of the bioreactor and disposed along a common rotational axis. A first arm has an end connected to the first mounting for rotation about the rotational axis and for pivoting about a first pivot axis that is transverse to the rotational axis. A second arm has an end connected to the second mounting for rotation about the rotational axis and for pivoting about a second pivot axis that is transverse to the rotational axis. Ends of the arms are coupled for pivoting about at least one additional pivot axis that is transverse to the rotational axis.

13 Claims, 6 Drawing Sheets

STIRRER FOR A BIOREACTOR

BACKGROUND OF THE INVENTION

1. Field of the Invention

The invention relates to a stirrer for bioreactors configured, in particular, as tanks having flexible walls, comprising a plurality of articulately connected arms which are jointly rotatable about a rotational axis, wherein a first arm is disposed rotatably about the rotational axis by its first arm end on a first mounting fastened to a first side of the tank.

2. Description of the Related Art

Stirrers are an essential part of bioreactors for homogenizing temperature and concentration differences. Moreover, the stirrers prevent cell deposition in bioreactors and disperse the air or gases in aerated bioreactors.

U.S. Pat. No. 2,045,710 A discloses a stirrer for a tank. The stirrer consists of a plurality of articulately connected arms, which in the elongated state can be slid into the tank through a tank opening, whereupon some side members open outward when contact is made with the tank bottom. A first arm is rotatable, jointly with the remaining arms connected thereto, about a rotational axis. The first arm is disposed rotatably by its first arm end on a first mounting, which is fastened, in the vertical direction, to a top side of the tank.

A drawback with the known stirrer is that with its bottom two arms, in the course of rotation, the bottom side of the stirrer rubs on the tank bottom. In the case of a metal tank, this rubbing produces unwelcome particles, while in the case of a tank made of plastic sheeting, the sheeting would be damaged after a short operating time. A horizontal or oblique operation is not possible with such a stirrer.

In addition, U.S. Pat. No. 6,769,800 B1 discloses a folding baffle system or a folding deflector apparatus, which is insertable into a tank or bioreactor through an opening which is smaller than the tank diameter. The baffle arrangement is made up of a plurality of rings and longitudinal segments or arms. The longitudinal segments, following the insertion into the tank, extend as they are set down and thus can come to bear against the tank walls as baffles. During stirring with a stirrer, the baffles then act as baffle plates or flow disturbers.

This baffle apparatus is not suitable for collapsing with a suitable tank, nor should a hint of a folding stirrer be inferred from this publication.

US 2002/0105856 A1 discloses a stirrer for bioreactors configured, in particular, as tanks having flexible walls. The stirrer has a flexible stirring tube, which on two opposite reactor walls which it breaches is statically held in static seals. In order to set the stirring tube between its two fixed ends in a type of rotary motion, a relatively rigid, spirally or helically configured drive shaft is introduced into the tube.

A drawback with this is that, for the subsequent introduction of a rigid shaft, the flexible hose must have guide bushings inside it to allow, on the one hand, the drive shaft to be fed in at all and, on the other hand, sufficient play to exist in relation to the flexible tube, which latter, in the course of its "rotary movements", is torn off or damaged at its fixed ends, which specifically cannot rotate.

The object of the present invention is therefore to provide a folding stirrer which is collapsible in a space-saving manner and can be inserted, in particular, into a tank having flexible walls.

SUMMARY OF THE INVENTION

This object is achieved by a stirrer with a plurality of arms articulated to one another and rotatable about a rotational axis. The arms include a first arm that has a first end that is fastened to a first mounting at a first side of the tank. The stirrer also has a last following arm facing away from the first arm and having a second arm end facing away from the first arm on a shaft of a second mounting rotatably about the rotational axis. The second mounting is fastened to a second side of the tank, which is opposite the first side of the tank. The arm ends connected articulatedly to the mountings or to the adjacent arm ends are respectively pivotable about a transverse axis disposed transversely to the rotational axis.

As a result of the arrangement of two mountings disposed on opposite end faces of the tank, unwelcome rubbing in the vertical direction against the bottom side of the tank is reliably avoided. Such a stirrer functions not only in a vertical position, but also in an oblique or horizontal position. The stirrer adapts to different heights of a tank and, as a flexible tank is filled, is pulled apart and opened with increasing tank volume. The stirrer here functions both in the partially opened and in the fully opened state.

According to a preferred embodiment of the invention, two arms are provided, the first arm being pivotably connected by its second arm end to the first arm end of the second arm, which forms the last following arm. Such a stirrer is of simple and compact construction and is suitable, in particular, for smaller and medium-sized tanks.

According to a further preferred embodiment of the invention, two mutually opposing arm pairs are provided. The first arm of each arm pair is pivotably connected by its first arm end to the first mounting and by its second arm end to the first arm end of the second arm, which forms the last following arm of the arm pair. The second arm of each arm pair is pivotably connected by its second arm end to the second mounting. Such a stirrer is just as flatly collapsible as a corresponding stirrer having only one arm pair, but has double the stirring area.

According to a further preferred embodiment of the invention, three arms are provided. The second arm is pivotably connected by its second arm end to the first arm end of the third arm, which forms the last following arm. The second end of the third arm is connected to the second mounting. Stirrers having three or more arms are suitable, in particular, for medium-sized and larger tanks.

According to a further preferred embodiment of the invention, the second arm disposed between the first arm and the third arm is the middle arm, and has double the length of the other arms. This stirrer is likewise suitable for larger tanks. Moreover, it is favorable that the stirrer is disposed symmetrically to the vertical rotational axis.

According to a preferred embodiment of the invention, the first mounting has a fixed base, which is fastened to the inner face of the first side of the tank. The first mounting has a shaft disposed rotatably in the base. The shaft has a first shaft end facing toward the tank interior, is pivotably connected to the first arm end of the first arm and a second shaft end facing away from the tank interior. The second shaft end is connectable to a drive shaft of a drive mechanism. Such a connection between the second shaft end and the drive shaft is possible, for example, via a connection socket, a screw joint or a latching mechanism. A magnetic coupling of the drive shaft to the second shaft end is also possible. Finally, the drive shaft can also pass directly into the second shaft end.

According to a further preferred embodiment of the invention, the second mounting likewise has a fixed base, which is fastened to the inner face of the second side of the tank, for example the bottom face. The second mounting has a shaft disposed rotatably in the base. The shaft has first and second shaft ends. The first shaft end of the second mounting faces toward the tank interior and is pivotably connected to the second arm end of the last arm. The second shaft end of the second mounting faces away from the tank interior and is mounted rotatably in the base. It is here particularly advantageous to weld the bases of the mountings to that side of the tank which respectively lies adjacent with said bases. For a low-friction rotation, the shafts, in a preferred embodiment, are mounted in the bases by slide bearings.

According to a further preferred embodiment of the invention, at least one of the arms has at least one stirring blade. If two arms are used, these have, for example, respectively on their outer sides facing away from each other, in each case two stirring blades. If three arms are used, the middle arm, insofar as it is at least twice as long as the two other arms, can have on its sides facing away from each other, respectively from the end to the middle, a convexly curved stirring blade. A collapse in one plane is then still possible.

According to a further preferred embodiment of the invention, a stirring blade, on the one hand, is pivotably coupled to the hinge joint between the first end of the last following arm and the second end of the adjacent arm and, on the other hand, is pivotably coupled to a first end of a guide rod, which by its second end is pivotably coupled to the second mounting and holds the stirring blade, given different distances between the mountings in the vertical direction, in the same horizontal position. Correspondingly, in the case of two mutually opposing arm pairs, it is possible for each arm pair to have a pivotable stirring blade, which is respectively held in the horizontal position by a guide rod.

According to a further preferred embodiment of the invention, a first blade mounting with a plurality of stirring blades, on the one hand, is pivotably coupled to the hinge joint between the first end of the last following arm and the second end of the adjacent arm and, on the other hand, is pivotably coupled to a first end of a guide rod, which by its second end is pivotably coupled to the second mounting and holds the first blade mounting with the stirring blades, given different distances between the mountings in the vertical direction, in the same horizontal position. As a result of the plurality of stirring blades on the first blade mounting, a better and more favorable mixing of the medium to be stirred or mixed is attained. It is additionally ensured that, at different fill states, in which the mountings have different distances apart, the mounting with its stirring blades is held in the same horizontal position.

According to a further preferred embodiment of the invention, in the case of three arms, a second blade mounting with a plurality of stirring blades, on the one hand, is pivotably coupled to the hinge joint between the first end of the second arm and the second end of the adjacent first arm and, on the other hand, is pivotably coupled to a first end of a second guide rod, which by its second end is pivotably coupled to the first blade mounting and holds the second blade mounting, given different distances between the mountings in the vertical direction, in the same horizontal position. It is hence possible, in the case of larger tanks, to dispose two blade mountings with respectively a plurality of stirring blades one above the other in the vertical direction and to hold them respectively in the vertical direction in the same horizontal position.

Further features of the invention emerge from the following detailed description and the appended drawings, in which preferred embodiments of the invention are illustrated by way of example.

DETAILED DESCRIPTION OF THE PREFERRED EMBODIMENTS

A stirrer 1 essentially consists of mutually connected arms 2, 3, a first mounting 4 and a second mounting 5.

Figure 1:
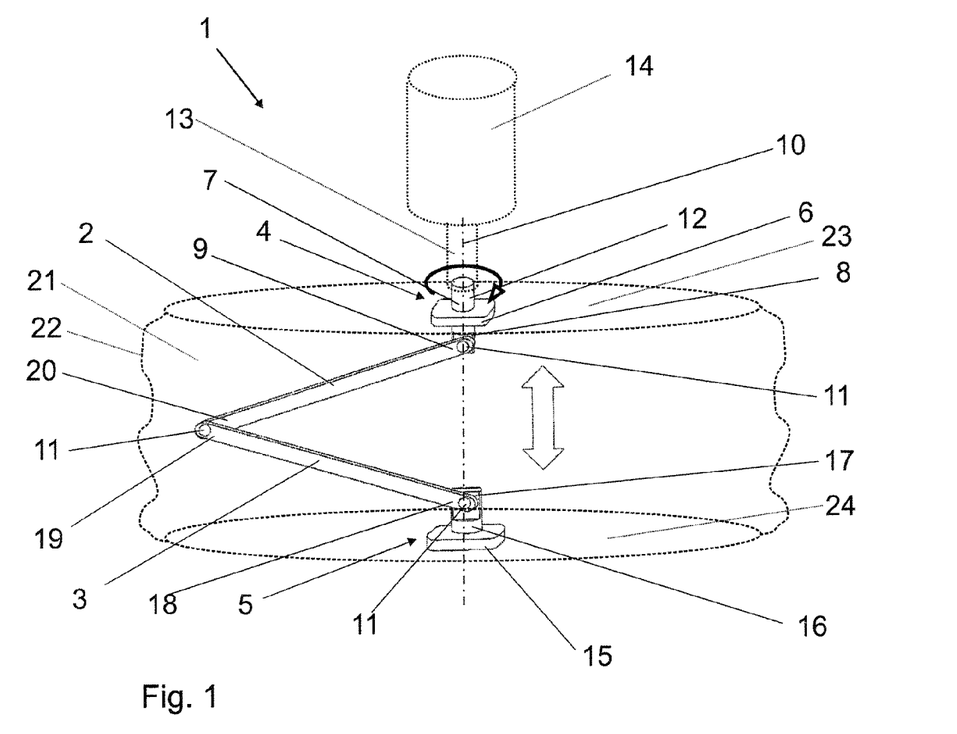
FIG. 1 is a perspective view of a folding stirrer having a flexible tank (indicated in dashed representation) and a drive mechanism with drive shaft (indicated in dashed representation).

The first mounting 4 has a fixed base 6, in which a shaft 7 is rotatably mounted. The shaft 7 has a first shaft end 8, which is connected to a first arm end 9 pivotably about a transverse axis 11 running transversely to a rotational axis 10. At its second shaft end 12 facing away from the first shaft end 8, the shaft 7 is connectable to a drive shaft 13 of a drive mechanism 14.

The second mounting 5 has a base 15, in which a shaft 16 is rotatably mounted. The shaft 16 is pivotably connected, at its first shaft end 17 facing toward the first mounting 4, to a second arm end 18 of the second arm 3. The second arm 3 is pivotably connected, at its first arm end 19 facing away from the second arm end 18, to a second arm end 20, facing away from the first arm end 9, of the first arm 2. The second arm 3 of the illustrative embodiments according to FIGS. 1, 2, 5, 6, 7 and 12 here respectively forms the last arm of the mutually pivotably connected arms 2, 3.

The arms 2, 3 can be rotated jointly with the shafts 7, 16 about the rotational axis 10.

When the stirrer 1 is installed in a bioreactor configured as a tank 21 having flexible walls, i.e. at least one flexible side wall 22, a first side 23, lying at the top in the vertical direction, and a second side 24, lying at the bottom in the vertical direction, it is fastened in the tank by welding of the base 6 of the first mounting 4 to the first side 23 and of the second base 15 of the second mounting 5 to the second side 24.

Figure 2:
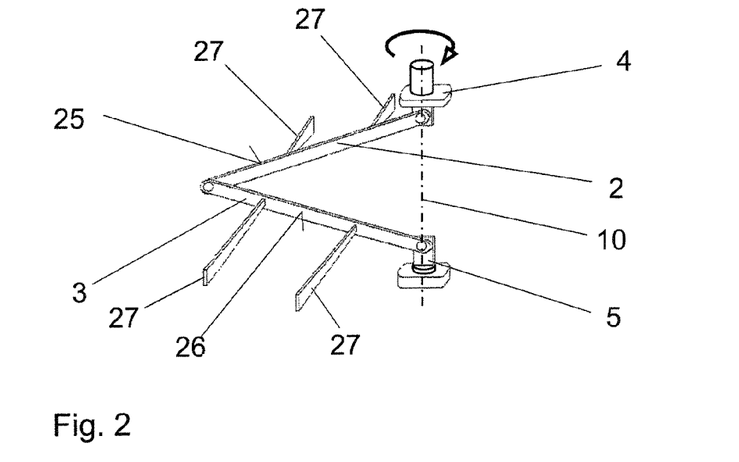
FIG. 2 is a perspective view of a folding stirrer having two arms, which respectively have two laterally disposed stirring blades.

In accordance with the illustrative embodiment of FIG. 2, the arms 2, 3 have respectively, on their outer sides 25, 26 facing away from each other, two stirring blades 27.

Figure 3:
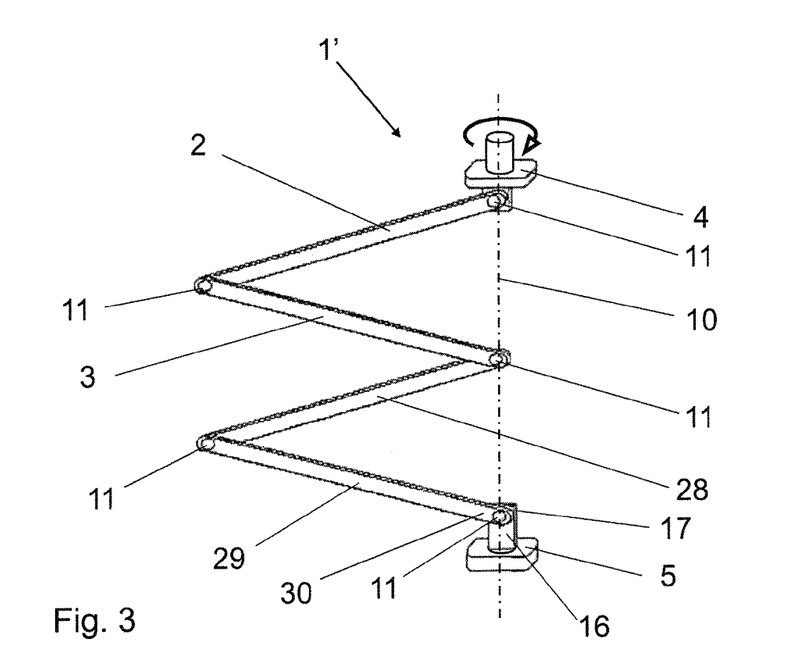
FIG. 3 is a perspective view of a folding stirrer having four arms.

The illustrative embodiment of FIG. 3 shows a stirrer 1', which has a first arm 2, a second arm 3, a third arm 28 and a fourth arm 29. The fourth arm 29 here forms the last arm, which by its second arm end 30 is connected to the first shaft end 17 of the shaft 16 of the second mounting 5 pivotably about the transverse axis 11.

Figure 4:
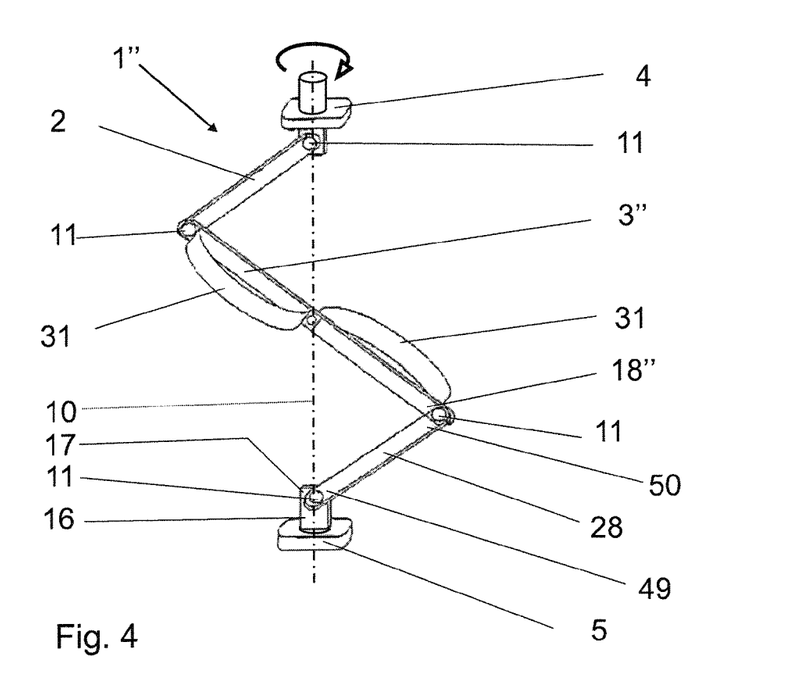
FIG. 4 is a perspective view of a folding stirrer having three arms, the middle arm having two stirring blades.

According to the illustrative embodiment of FIG. 4, the stirrer 1" has a first arm 2, a second arm 3" and a third arm 28. In this illustrative embodiment, the third arm 28 forms the last arm, and has a second end 49 pivotably connected to the second mounting 5. The second arm 3" is twice as long as its adjacent arms 2, 28. The second arm 3" bears on its two outer sides facing away from each other, offset by half its length, respectively a convexly shaped stirring blade 31. The third arm 28 is pivotably connected by its first end 50 to the second end 18" of the second arm 3".

Figure 5:
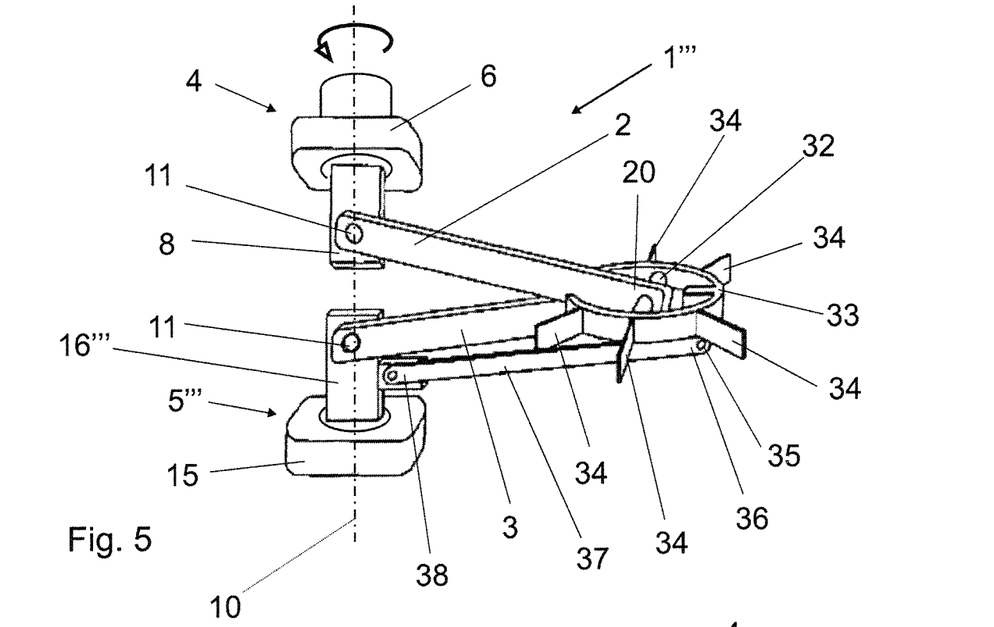
FIG. 5 is a perspective view of a folding stirrer having two arms and a blade mounting with a plurality of stirring blades.
Figures 6, 7:
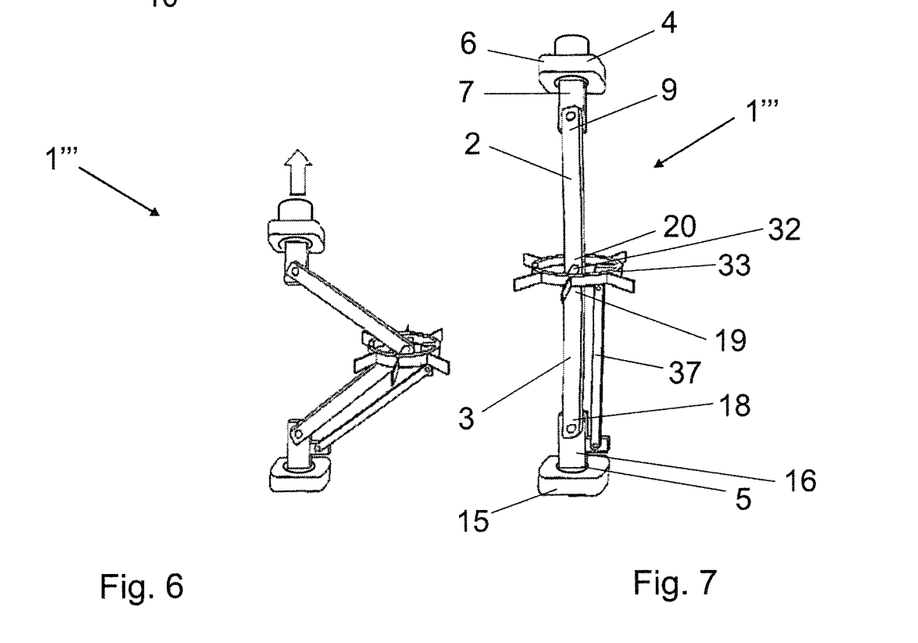
FIG. 6 is a perspective view of the stirrer of FIG. 5 in a further unfolded setting, in reduced representation.
FIG. 7 is a perspective view of the folding stirrer of FIG. 5 in a completely unfolded setting, in reduced representation.

The illustrative embodiment of FIGS. 5 to 7 shows a stirrer 1''', which on its hinge joint between the first arm 2 and the second arm 3 has a blade mounting 33, pivotable about a connecting shaft 32, for fastening a plurality of, in the illustrative embodiment six, stirring blades 34. The blade mounting 33 has a second coupling point 35 pivotably coupled to a first end 36 of a guide rod 37. The guide rod 37 runs roughly parallel to the second arm 3 and, has a second end 38 facing away from the first end 36 that is coupled to the shaft 16''' of the second mounting 5'''.

FIG. 6 shows the stirrer 1''' in a middle setting, and FIG. 7 shows the stirrer 1''' in a completely extended or unfolded setting.

Figure 8:
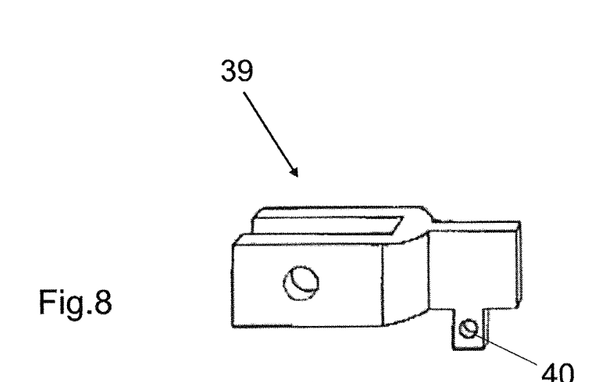
FIG. 8 is a perspective view of a mounting for stirring blades, having an outer coupling for a guide bar, in enlarged representation.

FIG. 8 shows a blade mounting 39 having an outer coupling point 40 for the mounting of a stirring blade (not represented).

Figure 9:
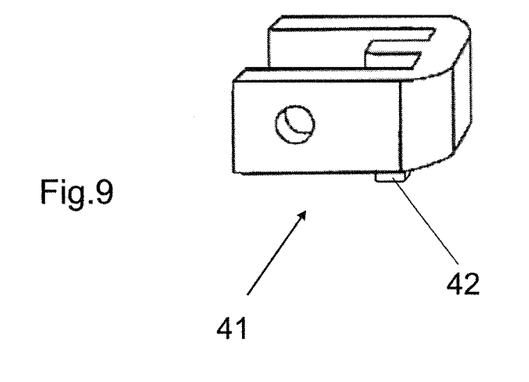
FIG. 9 is a perspective view of a mounting for stirring blades, having an inner coupling for a guide bar, in enlarged representation.

FIG. 9 shows a further blade mounting 41 having an inner coupling point 42.

Figure 10:
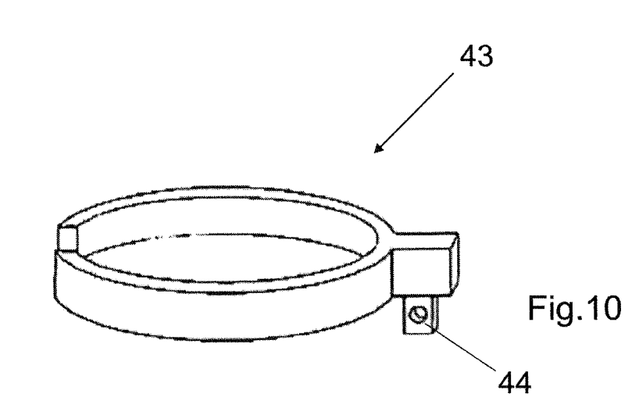
FIG. 10 is a perspective view of a further mounting for stirring blades, having an outer coupling for a guide bar, in enlarged representation.
Figure 11:
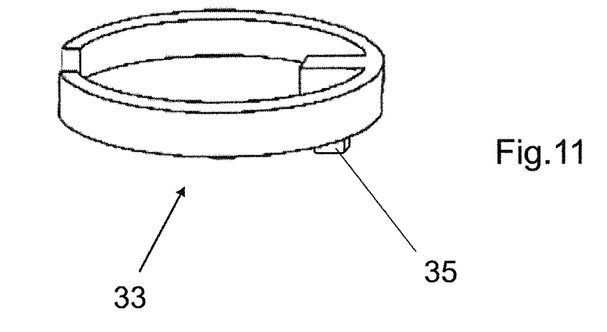
FIG. 11 is a perspective view of a further mounting for stirring blades, having an inner coupling for a guide bar, in enlarged representation.

FIG. 10 shows a further embodiment of a blade mounting 43 having an outer coupling point 44, and FIG. 11 shows the blade mounting 33 having the inner coupling point 35 in accordance with the illustrative embodiment of FIG. 5, yet without representation of the stirring blades.

Figure 12:
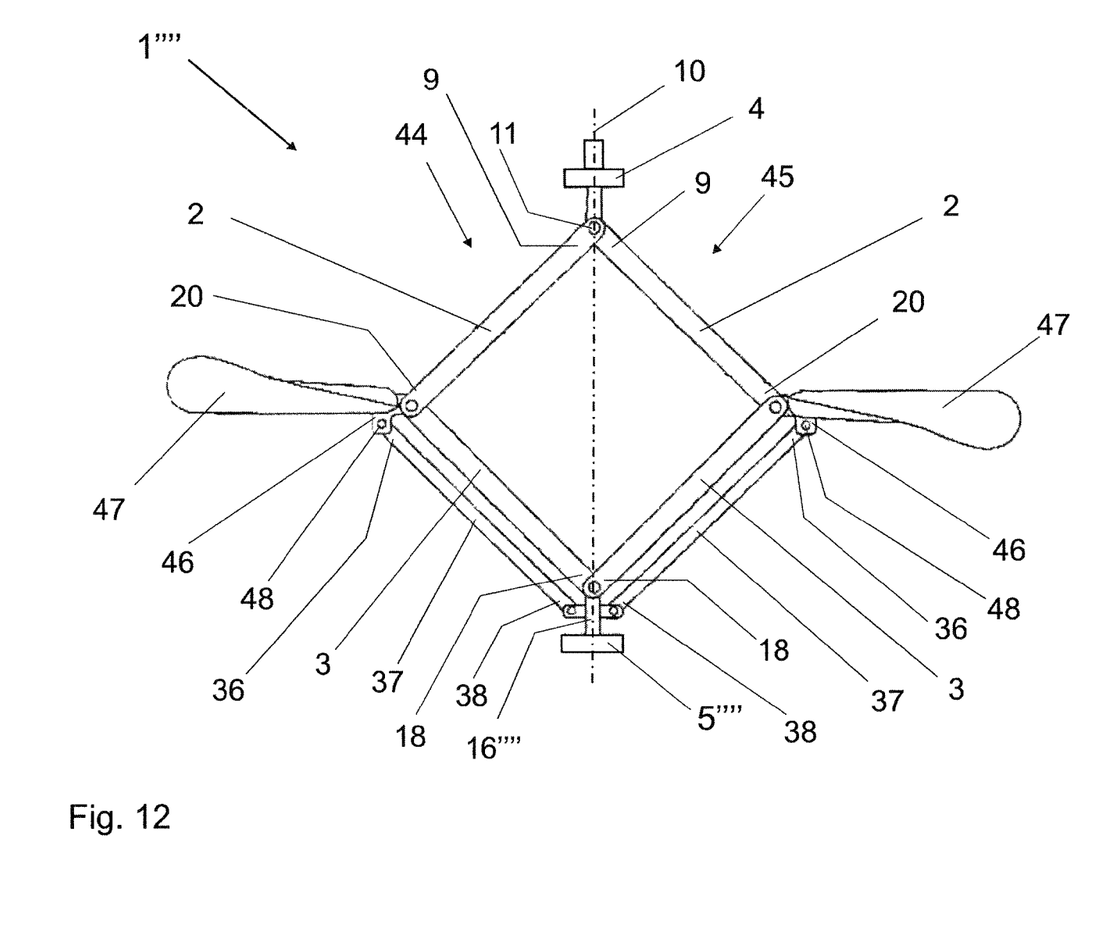
FIG. 12 is a side view of a folding stirrer having two mutually opposing arm pairs having respectively a stirring blade and attached guide bar.

The illustrative embodiment of FIG. 12 shows a stirrer 1''' having two mutually opposing arm pairs 44, 45. Each arm pair 44, 45 has on its hinge joint between the first arm 2 and the second arm 3 a blade mounting 46 with a stirring blade 47. The blade mounting 46 is connected by its coupling point 48 to the guide rod 37, which is pivotably coupled by its second end 38 to the shaft part 16'''' of the second mounting 5'''.

Figure 13:
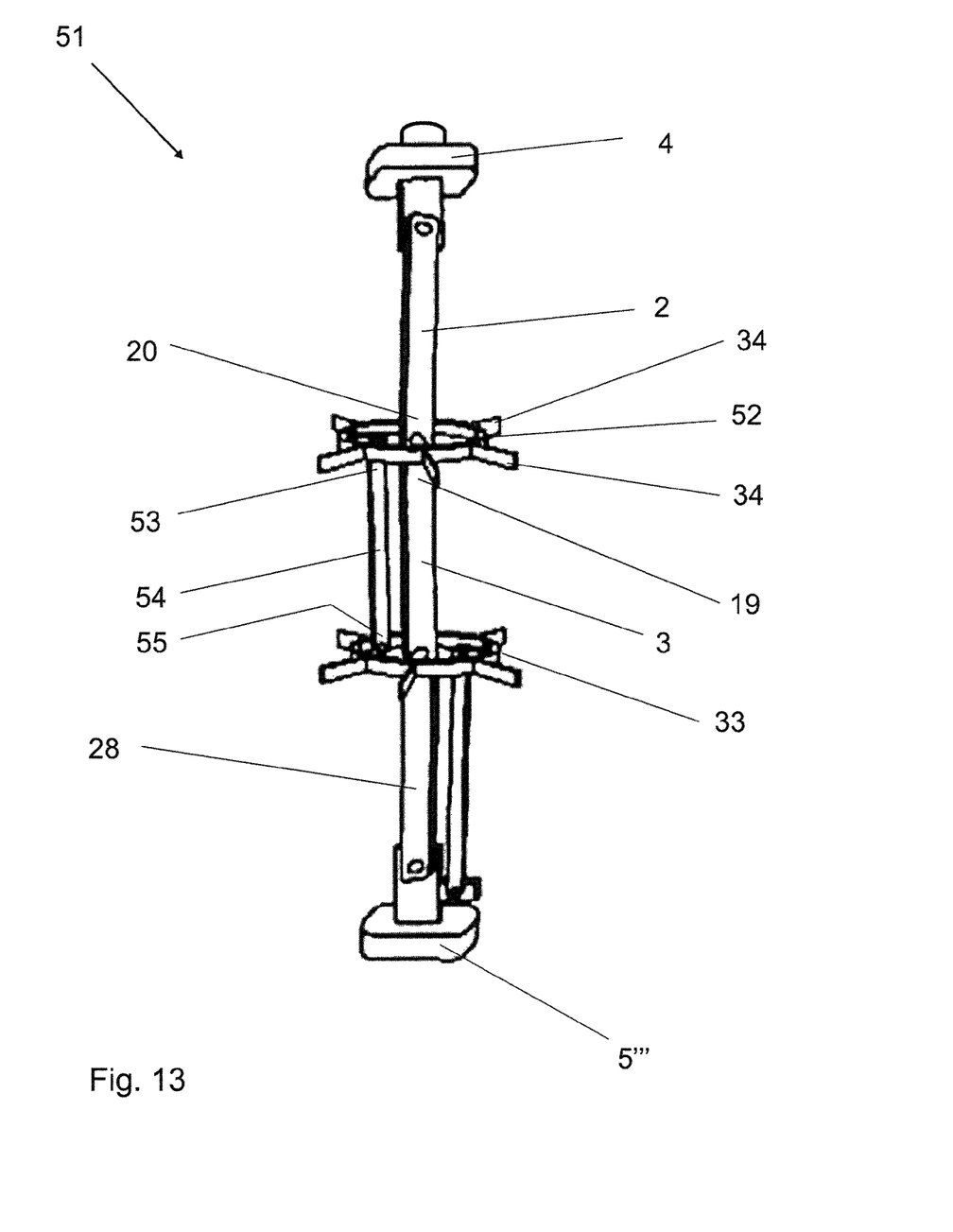
FIG. 13 is a perspective view of a folding stirrer having three arms and two blade mountings with a plurality of stirring blades.

The illustrative embodiment of FIG. 13 shows a stirrer 51 having three arms 2, 3, 28. The stirrer 51 has a second blade mounting 52 for a plurality of stirring blades 34. The second blade mounting 52 is pivotably coupled to the hinge joint between the first arm end 19 of the second arm 3 and the second arm end 20 of the adjacent first arm 2. On the other hand, the second blade mounting 52 also is pivotably coupled to a first end 53 of a second guide rod 54. The second guide rod 54 also has a second end 55 that is coupled pivotably to the first blade mounting 33 and holds the second blade mounting 52 with the stirring blades 34, in the same horizontal position given different distances between the mountings 4, 5''' in the vertical direction.

All embodiments of the invention thus have in common that the stirrer 1, 1", 1''', 1'''' disposed in a flexible tank 21, can be folded flat together with the tank 21 and, as the tank 21 is filled, is unfolded with the latter.

The invention claimed is:

1. A stirrer (1, 1', 1", 1''', 1'''') for bioreactor tanks (21) having flexible walls (22), the stirrer comprising: a plurality of articulately connected arms (2, 3, 28, 29) which are respectively pivotable about a transverse axis (11) and are jointly rotatable about a rotational axis (10), the plurality of arms including a first arm (2) with a first arm end (9) disposed on a first shaft (7) of a first mounting (4) fastened to a first side (23) of the tank (21), the first shaft (7) being rotatable about the rotational axis (10), the plurality of arms further including a last arm (3, 28, 29) having a first arm end (50) and a second arm end (18, 20, 30) opposite the first arm end (50) of the last arm (3, 28, 29), the second arm end (18, 20, 30) of the last arm (3, 28, 29) facing away from the first arm (2) and being disposed on a second shaft (16, 16''', 16'''') of a second mounting (5, 5''', 5'''') and the plurality of arms further comprising a second arm (3") with a second arm end (18) pivotably connected to the first arm end (50) of the last arm (3, 28, 29), the second mounting (5, 5''', 5'''') being fastened to a second side (24) of the tank (21) that is opposite the first side (23) of the tank (21), and the first arm end (9) of the first arm (2) and the second arm end (18) of the last arm (3, 28, 29) being connected respectively to the first and second shafts (7, 16, 16''', 16'''') so that the first and last arms (2; 3, 28, 29) are pivotable about transverse axes disposed transversely to the rotational axis (10).

2. The stirrer of claim 1, wherein the second arm (3") has a length at least double lengths of the first and last arms (2, 28) respectively.

3. The stirrer of claim 1, wherein the first mounting (4) has a first fixed base (6) fastenable to an inner face of the first side (23) of the tank (21), the first shaft (7) being disposed rotatably in the first base (6), the first shaft (7) having a first shaft end (8) facing toward an interior of the tank and being pivotably connected to the first arm end (9) of the first arm (2) and, the first shaft (7) having a second shaft end (12) facing away from the tank interior and being connectable to a drive shaft (13) of a drive mechanism (14).

4. The stirrer of claim 3, wherein the second mounting (5, 5''', 5'''') has a fixed base (15) fastenable to an inner face of the second side (24) of the tank (21), the second shaft (16, 16''', 16'''') being disposed rotatably in the base (15) and having a first shaft end (17) facing toward the tank interior and pivotably connected to the second arm end (18, 30, 49) of the last arm and, the second shaft (16, 16''', 16'''') having a second shaft end facing away from the tank interior and being mounted rotatably in the base part (15).

5. The stirrer of claim 4, wherein the bases (6, 15) of the mountings (4, 5) are the sides (23, 24) of the tank (21).

6. The stirrer of claim 4, wherein the shafts (7, 16) are mounted in the base parts (6, 15) by slide bearings.

7. The stirrer of claim 1, wherein at least one of the arms (2, 3, 28, 29) has at least one stirring blade (34).

8. The stirrer of claim 1 further comprising a first blade mounting (33) for a plurality of stirring blades, the first blade mounting (33) being pivotable coupled to a hinge joint between the second arm (3) and the last arm (28), a first guide rod having a first end pivotably coupled to the first blade mounting (33) at a location spaced from the hinge joint between the second arm (3) and the last arm (28) and having a second end pivotably coupled to the second mounting (5'''), and a second blade mounting (52) for a plurality of stirring blades (34), the second blade mounting (52) being pivotably coupled to a hinge joint between the second arm (3) and the first arm (2) and a second guide rod (54)

having a first end (53) pivotably coupled to the second blade mounting (52) at a location spaced from the hinge joint between the first arm (2) and the second arm (3) and a second end (55) pivotably coupled to the first blade mounting (33), so that the first and second guide rods hold the first and second blade mountings (33, 52) with the stirring blades (34) at a specified alignment to the rotational axis at different distances between the mountings (4, 5'''').

9. A stirrer (1, 1', 1'', 1''', 1'''') for bioreactor tanks (21) having flexible walls (22), the stirrer comprising:
a plurality of articulately connected arms (2, 3, 28, 29) which are respectively pivotable about a transverse axis (11) and are jointly rotatable about a rotational axis (10), the plurality of arms including a first arm (2) with a first arm end (9) disposed on a first shaft (7) of a first mounting (4) fastened to a first side (23) of the tank (21), the first shaft (7) being rotatable about the rotational axis (10), the plurality of arms further including a last arm (3, 28, 29) having a second arm end (18, 20, 30) facing away from the first arm (2) and being disposed on a second shaft (16, 16''', 16'''') of a second mounting (5, 5''', 5'''');
the second mounting (5, 5''', 5'''') being fastened to a second side (24) of the tank (21) that is opposite the first side (23) of the tank (21);
the first arm end (9) of the first arm (2) and the second arm end (18) of the last arm (3, 28, 29) being connected respectively to the first and second shafts (7, 16, 16''', 16'''') so that the first and last arms (2; 3, 28, 29) are pivotable about a transverse axis disposed transversely to the rotational axis (10); and
a stirring blade (47) pivotably coupled to a hinge joint between the last arm and an adjacent one of the arms and a guide rod (37) having a first end pivotably coupled to the stirring blade (47) at a location spaced from the hinge joint and a second end (38) pivotably coupled to the second mounting (5'''') so that the stirring blade (47) remains substantially perpendicular to an axis between the mountings at different distances between the mountings (4, 5'').

10. The stirrer of claim 9, wherein the first arm (2) has a second arm end (20) and the last arm has a first arm end (19) pivotably connected to the second arm end (20) of the first arm (2).

11. The stirrer of claim 10, wherein the first and last arms define a first arm pair (44), the stirrer further comprising a second arm pair (45) having first and last arms, the first arm (2) of the second arm pair (45) having a first arm end (9) pivotably connected to the first mounting (4) and having a second arm end (20) pivotably connected to a first arm end (19) of the last arm (3) of the second arm pair (45), and the last arm (3) of the second arm pair (45) having a second end (18) pivotably connected to the second mounting (5'''').

12. A stirrer (1, 1', 1'', 1''', 1'''') for bioreactor tanks (21) having flexible walls (22), the stirrer comprising:
a plurality of articulately connected arms (2, 3, 28, 29) which are respectively pivotable about a transverse axis (11) and are jointly rotatable about a rotational axis (10), the plurality of arms including a first arm (2) with a first arm end (9) disposed on a first shaft (7) of a first mounting (4) fastened to a first side (23) of the tank (21), the first shaft (7) being rotatable about the rotational axis (10), the plurality of arms further including a last arm (3, 28, 29) having a second arm end (18, 20, 30) facing away from the first arm (2) and being disposed on a second shaft (16, 16''', 16'''') of a second mounting (5, 5''', 5'''');
the second mounting (5, 5''', 5'''') being fastened to a second side (24) of the tank (21) that is opposite the first side (23) of the tank (21);
the first arm end (9) of the first arm (2) and the second arm end (18) of the last arm (3, 28, 29) being connected respectively to the first and second shafts (7, 16, 16''', 16'''') so that the first and last arms (2; 3, 28, 29) are pivotable about a transverse axis disposed transversely to the rotational axis (10); and
wherein a first blade mounting (33) for a plurality of stirring blades (34) is pivotably coupled to a hinge joint between the last arm and an end (20) of an adjacent one of the arms and a guide rod (37) having a first end pivotably coupled to the first blade mounting (33) at a location spaced from the hinge joint and a second end (38) pivotably coupled to the second mounting (5''') so that the first blade mounting (33) with the stirring blades (34) remains at a specified alignment to the rotational axis at different distances between the mountings (4, 5''').

13. A bioreactor, comprising:
a tank (21) having a top wall (23) with an inner surface, a bottom wall (24) with an inner surface facing the top wall (23) and a flexible side wall extending between the top and bottom walls (23, 24); and
a stirrer assembly (1) having a top mounting (4) fastened to the inner surface of the top wall (23) and having a top shaft (7) rotatable about a rotational axis (10), a bottom mounting (5) fastened to the inner surface of the bottom wall (24) and having a bottom shaft (16) rotatable about the rotational axis (10), a top arm (2) having opposite upper and lower ends, the upper end of the top arm being pivotably coupled to the top shaft (7) for pivoting movement about a top pivot axis transverse to the rotational axis (10), a bottom arm (28) having opposite upper and lower ends, the lower end of the bottom arm (28) being pivotably coupled to the bottom shaft (16) for pivoting movement about a bottom pivot axis substantially parallel to the top pivot axis and at least one pivotable coupling between the lower end of the top arm (2) and the upper end of the bottom arm (28) for articulation about at least one pivot axis substantially parallel to the top pivot axis, wherein the pivotable coupling between the lower end of the top arm (2) and the upper end of the bottom arm (28) comprises at least one intermediate arm.

* * * * *